(12) United States Patent
Nguyen

(10) Patent No.: US 10,007,934 B2
(45) Date of Patent: Jun. 26, 2018

(54) SYSTEM AND METHOD FOR SELF-PERFORMING A COSMETIC EVALUATION OF AN ELECTRONIC DEVICE

(71) Applicant: Tu Nguyen, Fremont, CA (US)

(72) Inventor: Tu Nguyen, Fremont, CA (US)

(73) Assignee: Greystone Data Technology, Inc., Fremont, CA (US)

( * ) Notice: Subject to any disclaimer, the term of this patent is extended or adjusted under 35 U.S.C. 154(b) by 0 days. days.

(21) Appl. No.: 15/097,251

(22) Filed: Apr. 12, 2016

(65) Prior Publication Data

US 2016/0225036 A1 Aug. 4, 2016

Related U.S. Application Data

(63) Continuation-in-part of application No. 14/474,262, filed on Sep. 1, 2014, now abandoned.

(60) Provisional application No. 62/027,096, filed on Jul. 21, 2014.

(51) Int. Cl.
| | |
|---|---|
| *G06Q 30/02* | (2012.01) |
| *H04N 5/225* | (2006.01) |
| *H04N 5/232* | (2006.01) |
| *G01N 21/88* | (2006.01) |
| *G06K 9/52* | (2006.01) |
| *G06K 9/62* | (2006.01) |
| *G06T 7/00* | (2017.01) |

(52) U.S. Cl.
CPC ......... *G06Q 30/0278* (2013.01); *G01N 21/88* (2013.01); *G01N 21/8851* (2013.01); *G06K 9/52* (2013.01); *G06K 9/6267* (2013.01); *G06T 7/0004* (2013.01); *H04N 5/2258* (2013.01); *H04N 5/23222* (2013.01); *H04N 5/23225* (2013.01); *G01N 2021/887* (2013.01); *G01N 2021/8858* (2013.01); *G01N 2021/8874* (2013.01); *G01N 2021/8877* (2013.01); *G06T 2207/30121* (2013.01)

(58) Field of Classification Search
CPC .............. G01N 21/88; G01N 21/8803; G01N 2021/8854
See application file for complete search history.

(56) References Cited

U.S. PATENT DOCUMENTS

| | | | | |
|---|---|---|---|---|
| 6,259,827 | B1 * | 7/2001 | Nichani | ................ G06T 7/0004 250/203.2 |
| 2004/0125208 | A1 * | 7/2004 | Malone | .............. H04N 1/32101 348/207.1 |
| 2005/0167620 | A1 * | 8/2005 | Cho | ....................... G01N 21/95 250/559.45 |
| 2010/0228676 | A1 * | 9/2010 | Librizzi | ................ G06Q 10/00 705/306 |

(Continued)

OTHER PUBLICATIONS

Misener, J. (Apr. 4, 2013). The 23 Most Important Mirror Selfies of All Time. Retrieved Jun. 24, 2016, from https://www.buzzfeed.com/jessicamisener/the-23-most-important-mirror-selfies-of-all-time.*

*Primary Examiner* — Noam Reisner

(74) *Attorney, Agent, or Firm* — Larisa Migachyov

(57) ABSTRACT

A system and method for cosmetic evaluation of an electronic device, using the device's own camera or cameras to take photos of the device itself using a mirror or mirrors and using the processor of the electronic device itself to analyze its own cosmetic condition.

24 Claims, 15 Drawing Sheets

(56) References Cited

U.S. PATENT DOCUMENTS

2013/0269013 A1* 10/2013 Parry .................. H04L 63/0861
 726/7
2013/0311318 A1* 11/2013 Librizzi ................ G06Q 10/00
 705/26.3
2014/0267691 A1* 9/2014 Humphrey .............. G06T 7/001
 348/125

* cited by examiner ated to the insurance industry. Currently, insurance companies only insure new electronic devices—it is easy to verify the condition of such a device. In order to insure a used electronic device, an insurance company would need to know the exact functional and cosmetic condition of the device. Since a method for objectively evaluating the cosmetic condition of a used electronic device in an unfalsifiable way does not currently exist, insurance companies do not insure used electronic devices.

SYSTEM AND METHOD FOR SELF-PERFORMING A COSMETIC EVALUATION OF AN ELECTRONIC DEVICE

CROSS-REFERENCE TO RELATED APPLICATIONS

The present application is a continuation in part of application Ser. No. 14/474,262, which takes priority from Provisional App. No. 62/027,096, filed Jul. 21, 2014, which is herein incorporated by reference.

BACKGROUND

Smartphones and other small electronic devices evolve rapidly, and thus are frequently upgraded by consumers. As a result, many consumers have one or more electronic devices that they no longer need. Reselling such devices is financially desirable.

In order to determine the value of an electronic device, its functional capacity and its cosmetic condition need to be evaluated. While evaluating a device's functional capacity usually only requires some simple electronics, evaluating the device's cosmetic condition requires either a human eye (and humans are often biased and inconsistent) or expensive and complex external camera systems. In situations where an electronic device is being repurchased automatically, at a kiosk, for example, the only option being used at present is expensive and complex external camera systems.

These systems are expensive; another drawback is that they are not available to a consumer in the home. There are many reasons why a consumer would want to evaluate the condition of a used electronic device at home without going anywhere: convenience, time savings, and so on. Therefore, this evaluation would have to be done without any external system, complex camera and connection to a computer.

There are apps on the market that evaluate the functional condition of an electronic device without requiring expensive and complex equipment (simply an app installed on the electronic device), but no apps exist for evaluating the cosmetic condition of an electronic device automatically. Typically, a consumer is asked to visually assess the cosmetic condition of their electronic device, which is subjective and vulnerable to lying by the consumer.

Since cosmetic evaluations are not standardized and not objective, it is difficult to trust a seller who is reselling a used electronic device; what the seller means by "like new" may not be what the consumer is expecting.

Another problem that exists due to the absence of reliable, objective cosmetic evaluations of a device is that related to the insurance industry. Currently, insurance companies only insure new electronic devices—it is easy to verify the condition of such a device. In order to insure a used electronic device, an insurance company would need to know the exact functional and cosmetic condition of the device. Since a method for objectively evaluating the cosmetic condition of a used electronic device in an unfalsifiable way does not currently exist, insurance companies do not insure used electronic devices.

A need exists for a system and method for evaluating the cosmetic condition of a used electronic device objectively, while not requiring any extra equipment beyond the electronic device itself. Further, a need exists for a system and method for evaluating the cosmetic condition of a used electronic results in an unfalsifiable way and certifying the accuracy of the results.

SUMMARY OF THE INVENTION

An object of the present invention is to provide a system and method for performing a cosmetic evaluation of an electronic device using the device's own built-in camera rather than an external camera system (which is expensive and complex) and using the processor of the electronic device itself to perform the calculation and evaluation of the cosmetic condition.

Another object of the present invention is to provide a method for performing a cosmetic evaluation of an electronic device that can be performed at home by a consumer.

Another object of the present invention is to provide a system and method for performing a cosmetic evaluation of an electronic device that uses the electronic device's own camera or cameras to take reference photos.

Another object of the present invention is to provide a system and method for performing a cosmetic evaluation of an electronic device that is reliable, objective, and unfalsifiable, by combining the analyzed images with unique device identification and other information.

The system of the present invention comprises an electronic device with a camera, and a first mirror, wherein the electronic device is configured to trigger the camera to take a photograph of the electronic device when it is placed in front of a first mirror in such a way as to reflect at least one surface of the electronic device into the camera's field of view, and to analyze the photograph to determine the number and type of cosmetic imperfections on that surface. The results may be transmitted to a server or displayed on the electronic device.

In an embodiment, the electronic device may comprise two cameras, and the processor is configured to trigger each camera to take a photograph of the device when it is placed in front of a mirror in such a way that each camera can take a photograph of the electronic device. Each photograph is then analyzed to determine the number and type of cosmetic imperfections on the surface.

In an embodiment, a second mirror may be used along with the first mirror in such a way as to reflect at least one of the right side, left side, top side, and bottom side of the device in such a way that it is in the camera's field of view. The processor is then used to trigger the camera to take a photograph of the device and the photograph is analyzed by the processor of the device to determine the number and type of cosmetic imperfections on the surface.

In an embodiment, the screen of the electronic device can display either a static image, a solid color, or be disabled, while a photograph is taken.

In an embodiment, the electronic device can display instructions for the user on how to place it in front of the mirror, and either take the photograph automatically when it is positioned correctly or instruct the user to take the photograph when it is positioned correctly.

In an embodiment, the method of the present invention comprises installing an application on the electronic device that triggers the electronic device to take a photograph when the electronic device is positioned in front of a mirror in such a way as to reflect an image of at least one surface of the electronic device, and that the processor of the device analyzes the photograph to determine the number and type of cosmetic imperfections on the surface, positioning a mirror in front of an electronic device in such a way that at least one camera of the electronic device faces the mirror, and using the camera to take a photograph of the electronic device. The photograph is then analyzed by the processor of the device to determine how many cracks, scratches, and other imperfections exist on the electronic device.

Since most electronic devices have a camera that is not dead-center to the electronic device, the electronic device may need to be tilted in order to capture an image of the entire device. The optimal tilt angle is preferably described by the relationship $\tan(\theta) < L/(50\% * H)$, where $\theta$ is the tilt angle, L is the length of the electronic device, and H is the height of the electronic device.

In an embodiment, the analysis step is performed by changing the contrast on the photograph to make any imperfections more visible, counting the number of scratches and wear marks and determining the length of each, and using that information to produce a cosmetic condition score.

Some electronic devices have a second camera. In an embodiment, the method of the present invention comprises positioning a mirror in front of an electronic device in such a way that the second camera faces the mirror and using the second camera to take a photograph of at least one surface of the electronic device; then positioning the mirror (or the electronic device) in such a way that the first camera faces the mirror and using the first camera to take a photograph of at least one surface of the electronic device. Then, both photographs are analyzed by the processor of the device to determine how many cracks, scratches, and other imperfections exist on the electronic device.

In an embodiment, a second mirror is positioned in such a way as to reflect at least one of the sides of the device in a way that at least one camera of the electronic device can take a photograph of at least one of the sides of the device. Then, that photograph is analyzed by the processor of the device to determine how many cracks, scratches, and other imperfections exist on the electronic device.

In an embodiment, the screen of the electronic device is prevented from showing an image of what is "seen" by the camera. Instead, it can show another image or a solid color, said image or solid color being intended to show any scratches, cracks, or other imperfections on the screen on the device more clearly than the image of what's in front of the camera.

The analysis step preferably comprises changing at least one visual parameter of the photograph to make any imperfections more visible, counting the number of imperfections in the photograph and determining the length of each imperfection, and using this information to produce a cosmetic condition score. In an embodiment, different weighting can be ascribed to cracks, scratches, and wear marks. In another embodiment, different weighting can be ascribed to imperfections on the sides of the device versus imperfections on the screen of the device.

In an embodiment, the method of the present invention comprises a series of steps to determine whether a crack on the screen of the device affects the LCD screen, or whether it is a superficial crack that only affects the glass cover. If a crack on the screen of the device affects the LCD screen, the solid color or static image background will show some imperfections, either around the area of the crack, or elsewhere, due to the leakage of the liquid crystals. If the crack is superficial, the LCD screen will show no imperfections.

In an embodiment in which at least one photograph shows the screen of the device, wherein the electronic device displays a background image of checks of a first color and a second color, the analyzing step comprises creating an image mask (by applying a filter of the first color to create a first color-filtered image, applying a filter of the second color to create a second color-filtered image, and merging the two and inverting to create an image mask); identifying and isolating the screen of the electronic device in the photograph to create a screen image and performing the same procedure on the screen image; using an edge detector algorithm on the screen image to create a processed screen image and merging it with the result; subtracting the mask image; and applying an edge detector algorithm to the result image. If any edges are found, the system can simply circle them, or analyze further to determine whether these edges are cracked glass or scratches. If an edge extends all the way to the edge of the screen, it is considered cracked glass; if an edge does not, it is considered a scratch.

In an embodiment in which at least one photograph shows an image of the screen of the device, wherein the electronic device displays a background image of checks of a first color and checks of a second color, the analyzing step comprises identifying and isolating the screen of the device to produce a screen image, applying a colored filter of the first color to the screen image to produce a first color-filtered screen image, applying a colored filter of the second color to the screen image to produce a second color-filtered screen image, and merging the first color-filtered screen image and the second color-filtered screen image with an OR function to create a merged image. If any pixels in the merged image are black, it is concluded that the electronic device has a damaged LCD screen.

In an embodiment, the user is instructed on how to place the mirror or mirrors properly, or how to place the device in front of the mirror or mirrors, in order to take the pictures correctly. The instructions can be given visually (i.e. by images shown on the screen of the device), auditorially (via the speaker or earphone of the device), or by vibration (i.e. the device vibrates when it is placed correctly), or in any combination of these.

In an embodiment, the photograph or photographs are taken automatically when the device is at a particular distance from the mirror or mirrors and/or at a particular angle to the plane of the mirrors. The distance is preferably the closest focal distance from the camera that is taking the photograph.

In an embodiment, the user is instructed to perform an action to take the photograph when the device is at a particular distance from the mirror or mirrors. The action can be pressing a button, interacting with the touchscreen, or any other action.

In an embodiment, some information is encoded in the at least one photograph. This information may comprise the device unique identification, a time and date of the photograph, a visual parameter of the photograph, and the name of the owner of the electronic device. The information may be prepended to the image data, postpended to the image data, or steganographically enclosed in the image data. The information may also be encrypted.

LIST OF FIGURES

DETAILED DESCRIPTION OF THE PREFERRED EMBODIMENT

The present invention may be used with any electronic device that comprises a camera and a processor and memory and that can run apps. Preferably, the electronic device is a smartphone, but it may also be a tablet, laptop, mp3 player, e-reader, or any other similar electronic device.

Figure 1:
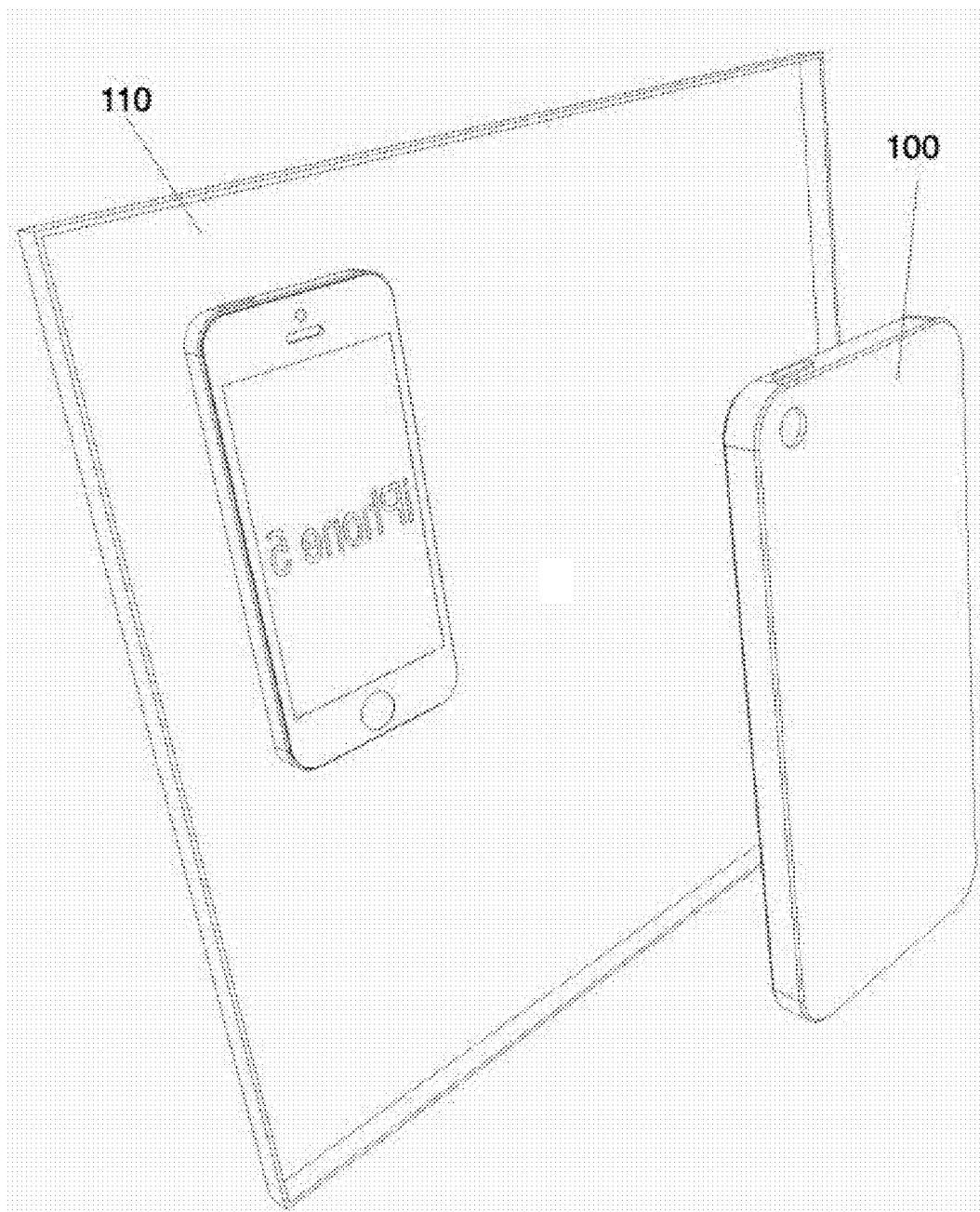
FIG. 1 shows a diagram of an electronic device being used to practice the method of the preferred embodiment of the present invention.
Figure 2:
FIG. 2 shows a sample install screen for the app of the present invention.

FIG. 1 shows a diagram of an electronic device 100 being used in front of a mirror 110 to take a picture of itself. The camera of the electronic device 120 is triggered either manually or automatically when the electronic device 100 is placed in front of the mirror 110. In the preferred embodiment, the electronic device 100 comprises an app that instructs the user on proper mirror placement and automatically takes a photo or photos when the electronic device and mirror are in correct relative positions. FIG. 2 shows an install screen for an embodiment of the app.

In the preferred embodiment, the app performs at least the following functions: instructing the user on correct positioning of the electronic device in front of the mirror (or the mirror in front of the electronic device), taking the photo or photos (either automatically or manually) when the electronic device is correctly positioned, and analyzing the photo or photos for cracks, scratches, or other imperfections.

Figure 3A:
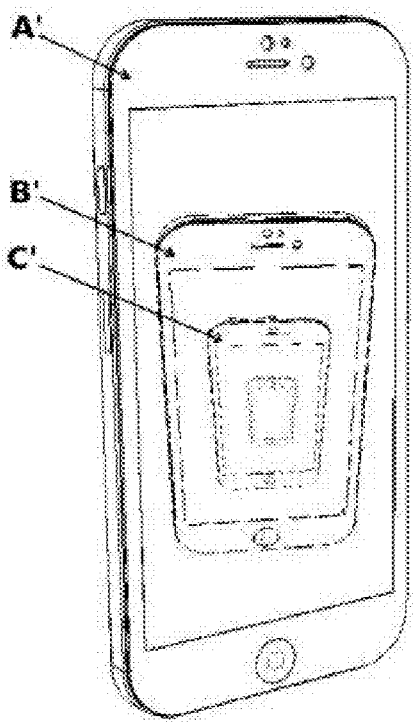
FIG. 3A shows recursive images resulting from not disabling the screen while the front camera is operating.
Figure 3A:
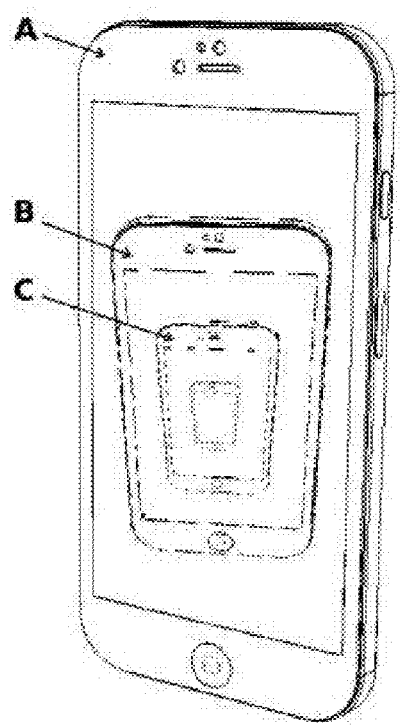
Figure 3B:
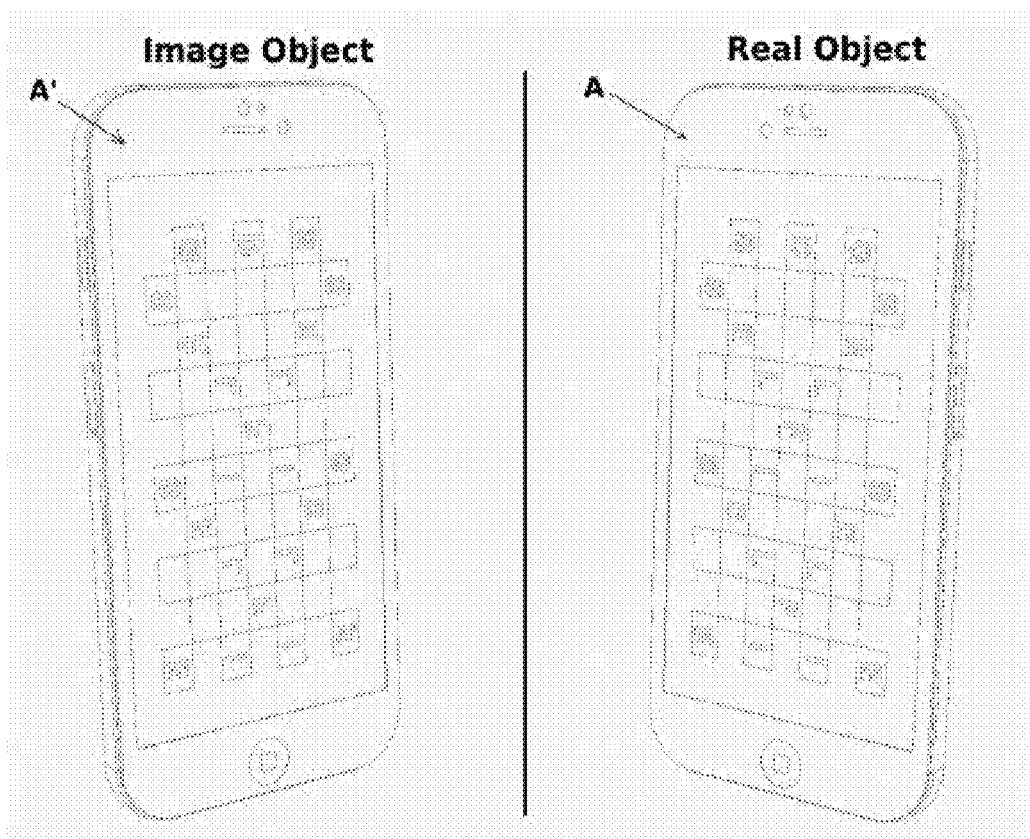
FIG. 3B shows a device used to take a picture of itself with the screen showing a static image.

Typically, when a front-facing camera of a device is used to take a photo, the screen of the device shows what the camera is "seeing". This causes trouble when the front-facing camera is used to take a photo of the electronic device itself in a mirror; FIG. 3A shows what happens when the screen of the device is allowed to show what the camera is "seeing" in that scenario. Object A creates an image A' in the mirror; the camera captures the image A' and shows it as B (on the screen). Then, the object AB creates the image of A'B'; the camera captures that and creates the image of B and C on the screen. This creates the image of A'B'C', and so on. The recursive image shown in FIG. 3A can obscure any imperfections in the device screen and make it harder to analyze the photo to determine the condition of the device screen. Thus, the preferred embodiment disables this function of the screen when the front-facing camera is used to take a photo of the electronic device. FIG. 3B shows the front-facing camera of the device used to take a photo of the device with the screen disabled and showing a static image.

Figure 12:
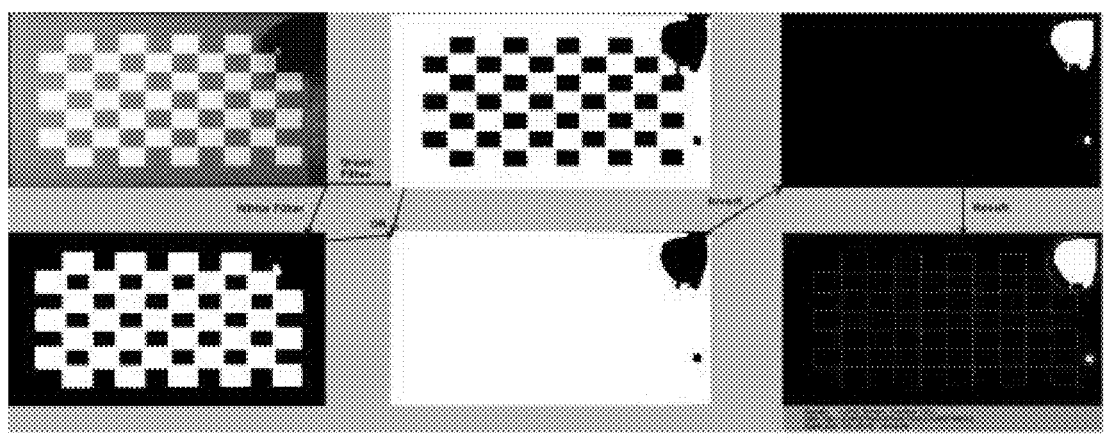
FIG. 12 shows a series of images showing the detection of a broken LCD screen.
Figure 14:
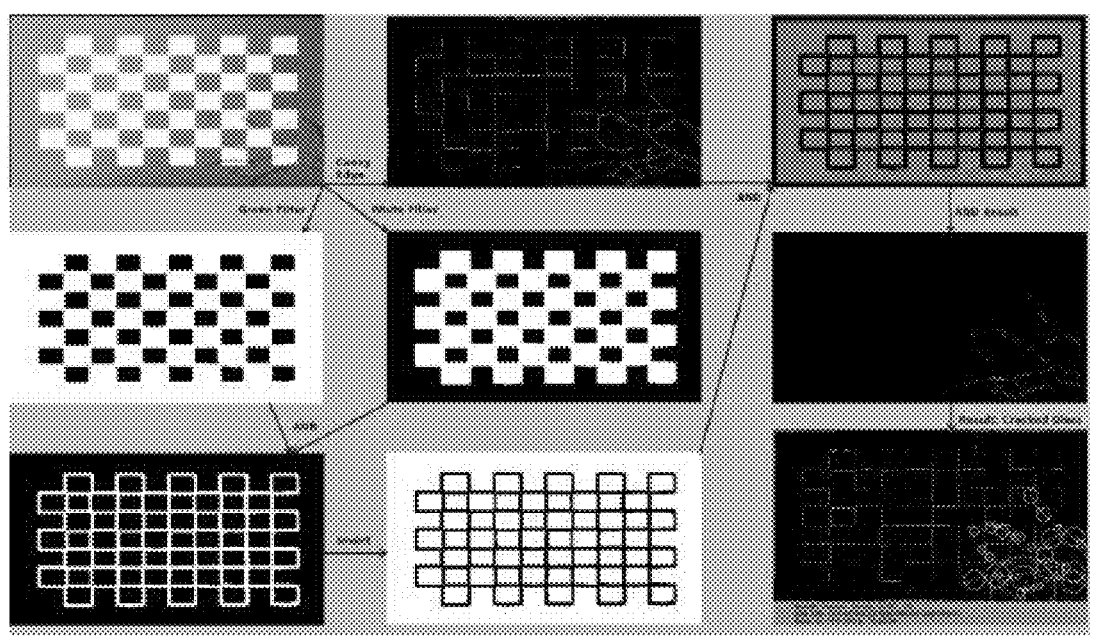
FIG. 14 shows a series of images showing the detection of cracked glass.

When the screen is disabled, it could simply be left turned off, or could show a solid color or a static image. For example, the screen could show a solid white background, which could easily show any cracks or other cosmetic imperfections in the glass or any imperfections in the LCD itself. However, any other image could be used. For example, the screen could show a grid, as shown in FIG. 3B, so that any imperfections in the LCD screen could show up as distortions of the gridlines. In the preferred embodiment, the screen shows a green and white checkerboard pattern, as shown in FIGS. 12 and 14.

Figure 4:
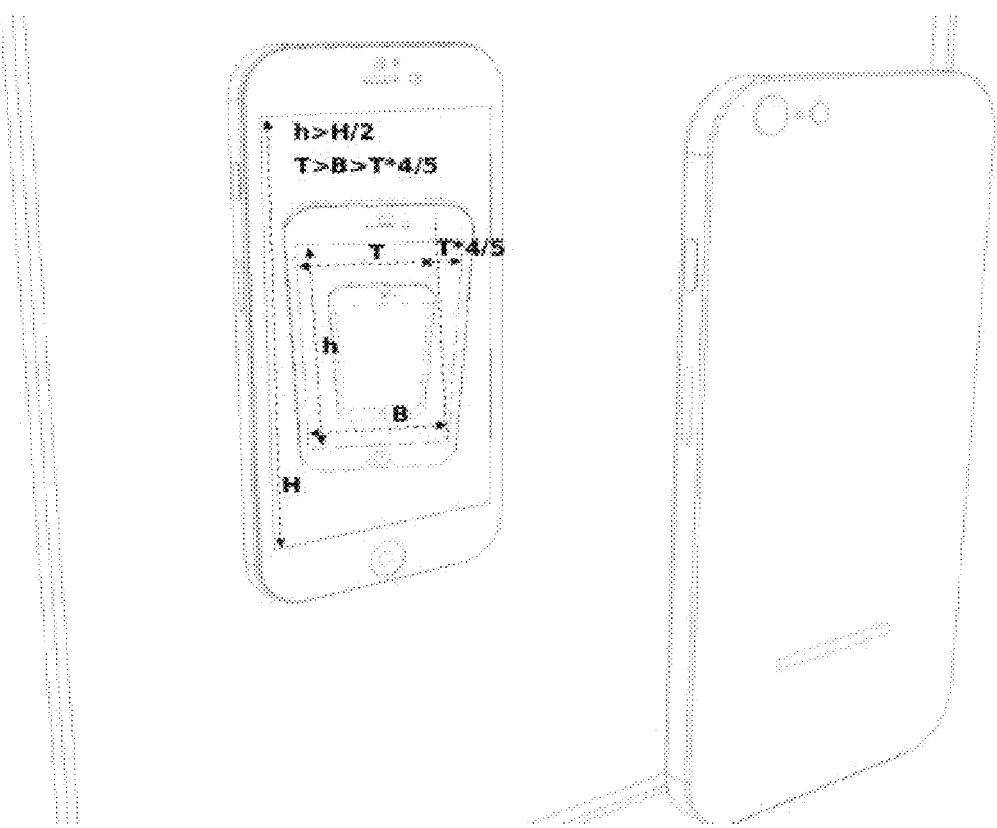
FIG. 4 shows sample instructions given to the user on how to position the device in front of a mirror.

The app may instruct the user on how to position the electronic device to take the photograph, as shown in FIG. 4. Once the electronic device is positioned correctly, the app may either trigger the device to take the picture automatically or instruct the user to take the picture.

Figure 5:
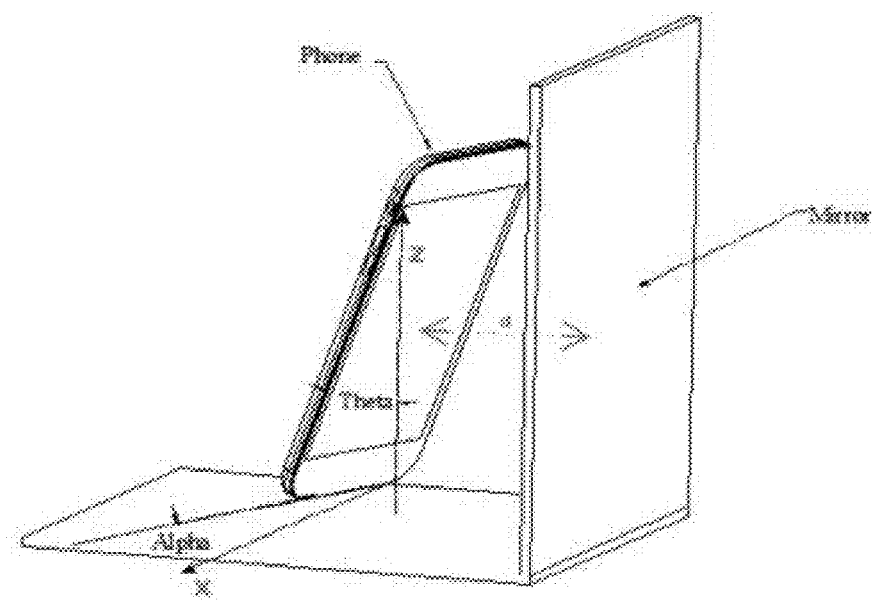
FIG. 5 shows an electronic device positioned at an angle to the mirror for the best image.

Since in most cases, the camera is not dead-center on the device, the user may need to tilt the electronic device at an angle in order for the camera to "see" the entire electronic device, as shown in FIG. 5. The exact angle of tilt depends on the camera placement on the particular electronic device being photographed. As shown in the Figure, the device may need to be tilted in several directions in order to obtain the best and least distorted picture.

As shown in FIG. 5, the dimensions that matter for the placement of the electronic device in front of the mirror are:
  a. d, the distance from the electronic device to the mirror;
  b. $\theta$, the angle between the electronic device and the z-axis;
  c. $\alpha$, the angle between the electronic device and the x-axis.

FIG. 4 shows the parameters of the image, as labeled:
  a. H: height of the real LCD screen;
  b. h: height of the LCD screen in the image;
  c. L: width of first image LCD screen at top (Longer)
  d. S: width of first image LCD screen at bottom (Shorter)

A user would move and tilt the electronic device relative to the mirror to vary these three parameters. For optimal results, the best parameters are:
  a. 5 cm (2 in)<d<10 cm (4 in)
  b. h>H*50% (optimal)
  c. S>L*80% (optimal)
  d. 0°<$\theta$<8°
  e. 0°<$\alpha$<3°

Figure 6:
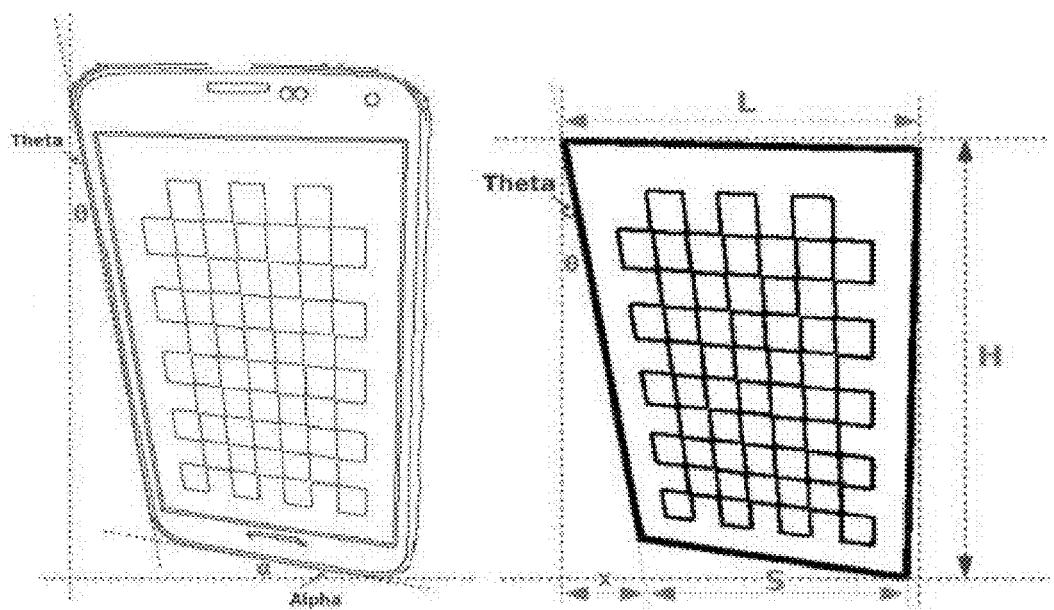
FIG. 6 shows the optimal ratio of the short side to the long side in the photo of the electronic device.

FIG. 6 shows a distorted image of a rectangular screen obtained by taking the photograph of a tilted device as shown in FIG. 5. For the image processing software to work effectively, it is optimal if the short side S is greater than ⅘ or 80% the length of the long side L; furthermore, it is optimal if:
  a. $\tan(\theta)=x/H \rightarrow x=H*\tan(\theta)$
  b. S>L*80%*******x=L−S Therefore x<L*20%
  c. ==>$\tan(\theta)<L/(50\%*H)$ optimal condition
  d. $\tan(\theta)<L/(50\%*H)$ In the case of an iPhone 5, for example, which has the dimensions of 123.8×58.6×7.6, L/H=58.6/123.8:
  a. $\tan(\theta)<58.6/123.8/5=0.0947$
  b. $\theta<\arctan(0.0947)=5.4°$ These parameters will obviously be different for different phones or other electronic devices.

Figure 7:
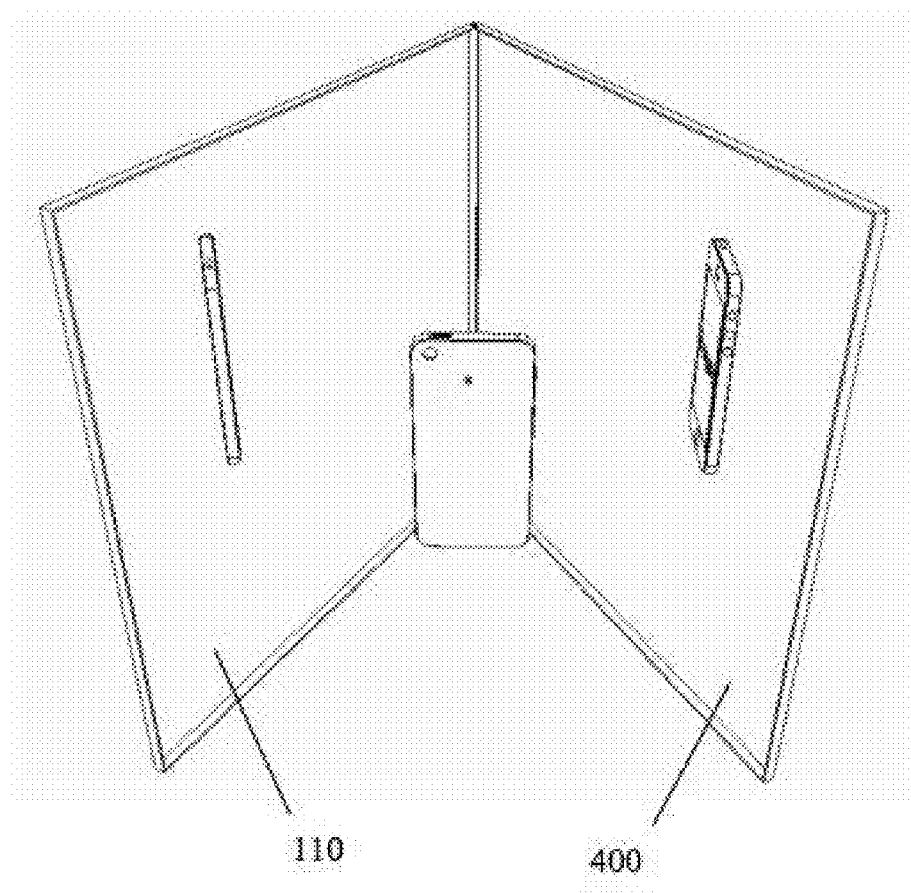
FIG. 7 shows two mirrors used to take photos of the sides of the device.

In an embodiment, the system and method of the present invention can also take photos of the sides of the electronic device. To do that, the user is instructed to place a second mirror 400 next to the device as shown in FIG. 7. The second mirror 400 reflects the sides of the device in a way that is visible to the front-facing camera. The front-facing camera is then used to take the photo. Alternately, the rear-facing camera or any other camera of the device could be used as well.

Figure 8:
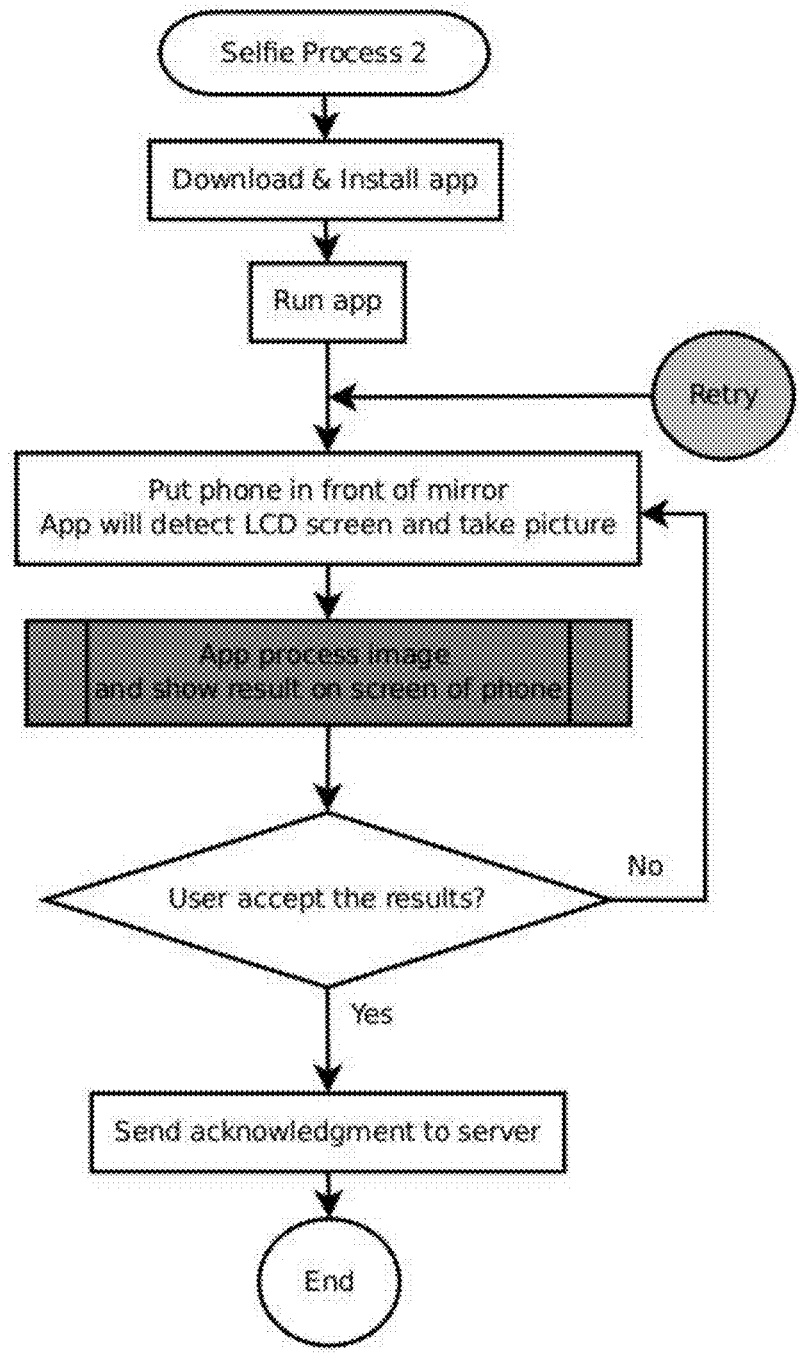
FIG. 8 shows a flowchart of the method of the present invention.

FIG. 8 shows a flowchart of the operation of the method of the present invention. First, the user has to download and install the app and run it. The app can be loaded OTA (over the air) or in any other manner suitable for loading apps. The user is then prompted by the app to put their electronic device in front of a mirror; the app will detect the LCD screen and take a picture. (In other embodiments that are not shown, the app may prompt the user to place multiple mirrors around the device or to take multiple pictures). After the photograph or photographs are taken, the app analyzes the image using the processor of the electronic device itself (the analysis steps will be discussed later) and shows the results to the user on the screen of the electronic device. If the user accepts the results, an acknowledgment is sent to the server and the process concludes.

The resolution of the photographs is preferably high enough to show cracks and scratches, but not so high that the analysis of the photographs could not be done on the electronic device itself in a reasonable amount of time. In the preferred embodiment, the resolution is 1600×1200 pixels or 1920×1080 pixels, depending on the desired image proportions (4:3 or 16:9). If the resolution of the camera is higher than the above numbers, the image will be scaled to that size.

In an embodiment, the app also steganographically encodes data about the device in the device photo or photos. Such data may include the device unique identification or serial number, the name and address of the owner of the device, the date and time of the photo, some parameter of the photo itself (i.e. the number of blue pixels in the photo), and so on. This helps ensure that the photos of the device are authentic and not falsified by an unscrupulous user.

Figure 9:
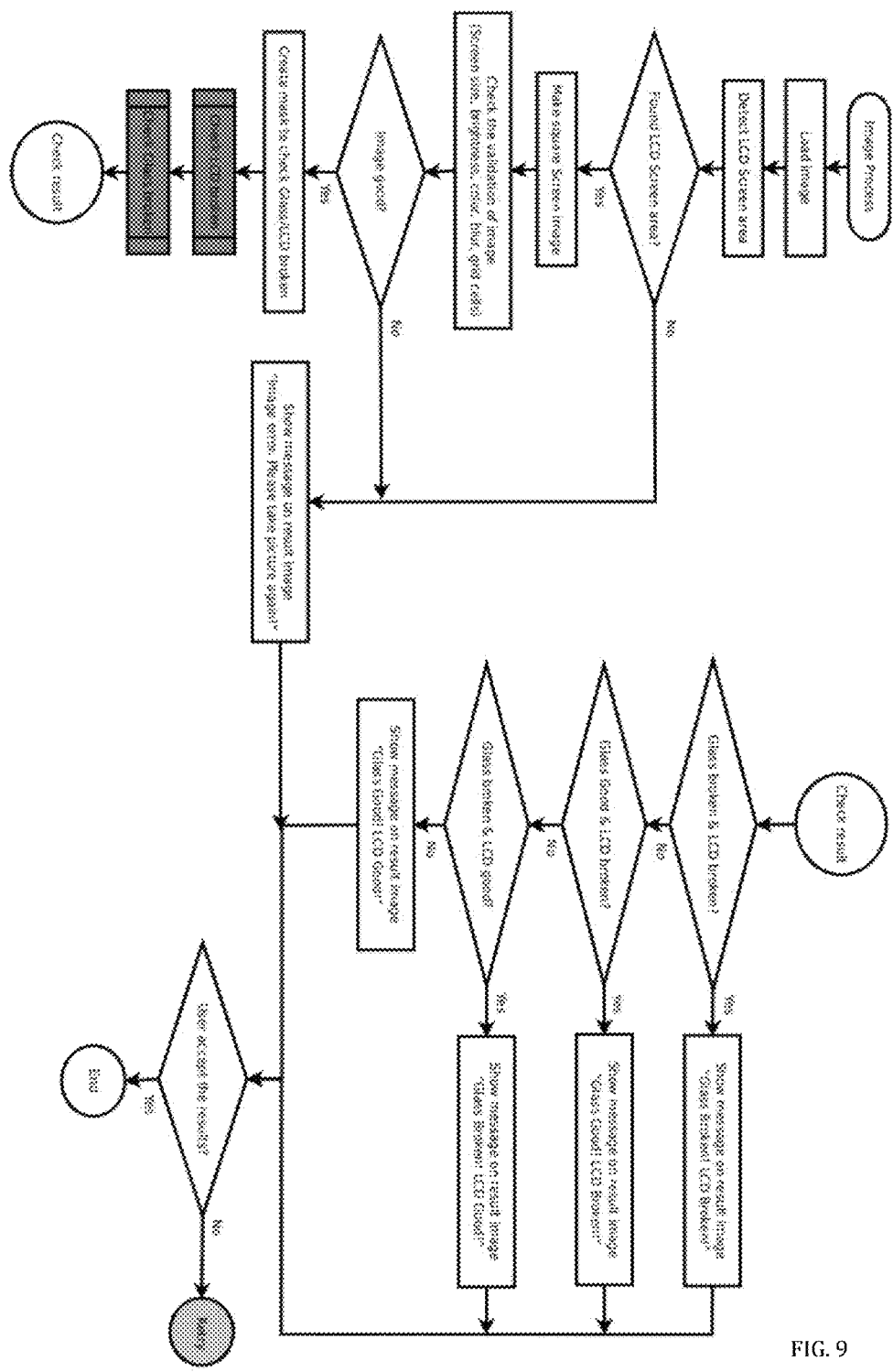
FIG. 9 shows a more detailed flowchart of the image processing method of the present invention.

After the photos are taken, they are analyzed. This step is preferably performed on the device itself. FIG. 9 shows a flowchart of the analysis process, concentrating on the front side of the device (with the LCD screen). Similar analysis processes could be used for other sides of the device, except that the steps relating to the LCD screen could be omitted.

As shown in FIG. 9, first the image is loaded and the LCD screen area is detected. If the LCD screen area is not found, an error message is displayed for the user and the user is instructed to position the electronic device again to take the picture again. If it is found, the image is processed and stretched to make it rectangular, and the screen size, brightness, color, blur, and grid cells are checked. If any parameters are unacceptable, an error message is displayed. If the image is good, a mask is created to check the LCD screen and to determine whether or not the glass is cracked. Then, depending on the condition of the LCD screen and the glass, a message is displayed for the user.

Figure 10:
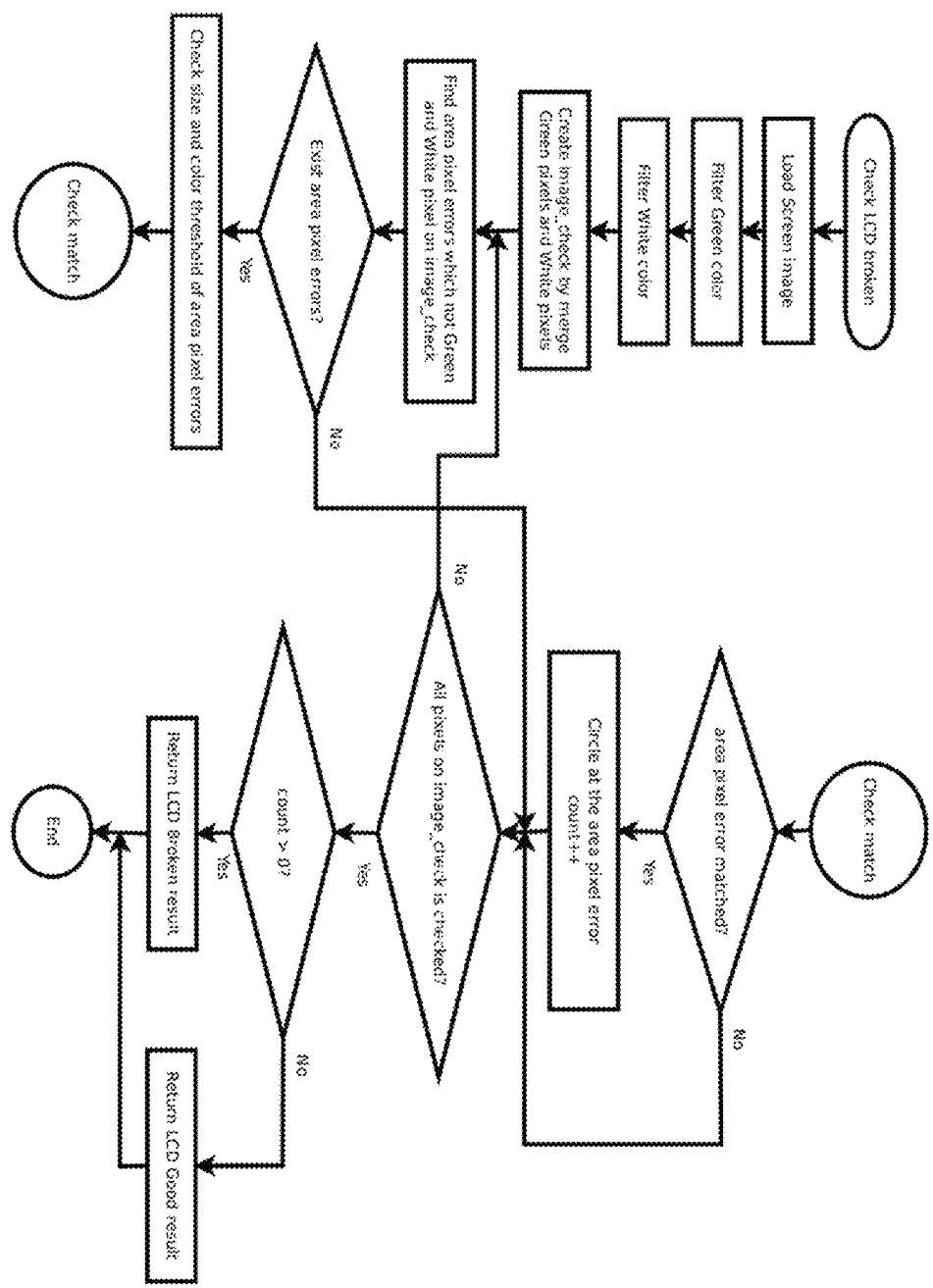
FIG. 10 shows a flowchart of the method of checking for broken LCD screens of the present invention.

FIG. 10 shows a flowchart of the process for checking whether the LCD screen of the device is broken. The screen image is loaded. In the preferred embodiment, the screen shows a green and white checkerboard pattern. The part of the image showing the screen is isolated and reshaped into a rectangle for ease of processing. This is preferably done by finding the four vertices of the LCD screen in the image and squaring it using the perspective transformation function of the OpenCV library (warpPerspective( )). Then, a green filter is applied to the image and the green-filtered image is saved. A white filter is then applied to the same image and the white-filtered image is saved. Then, the two images are combined with an OR function—i.e. any pixels that are white in either image are marked as white. Any black pixels in the resulting combined image then mean that the LCD screen is broken.

Figure 11:
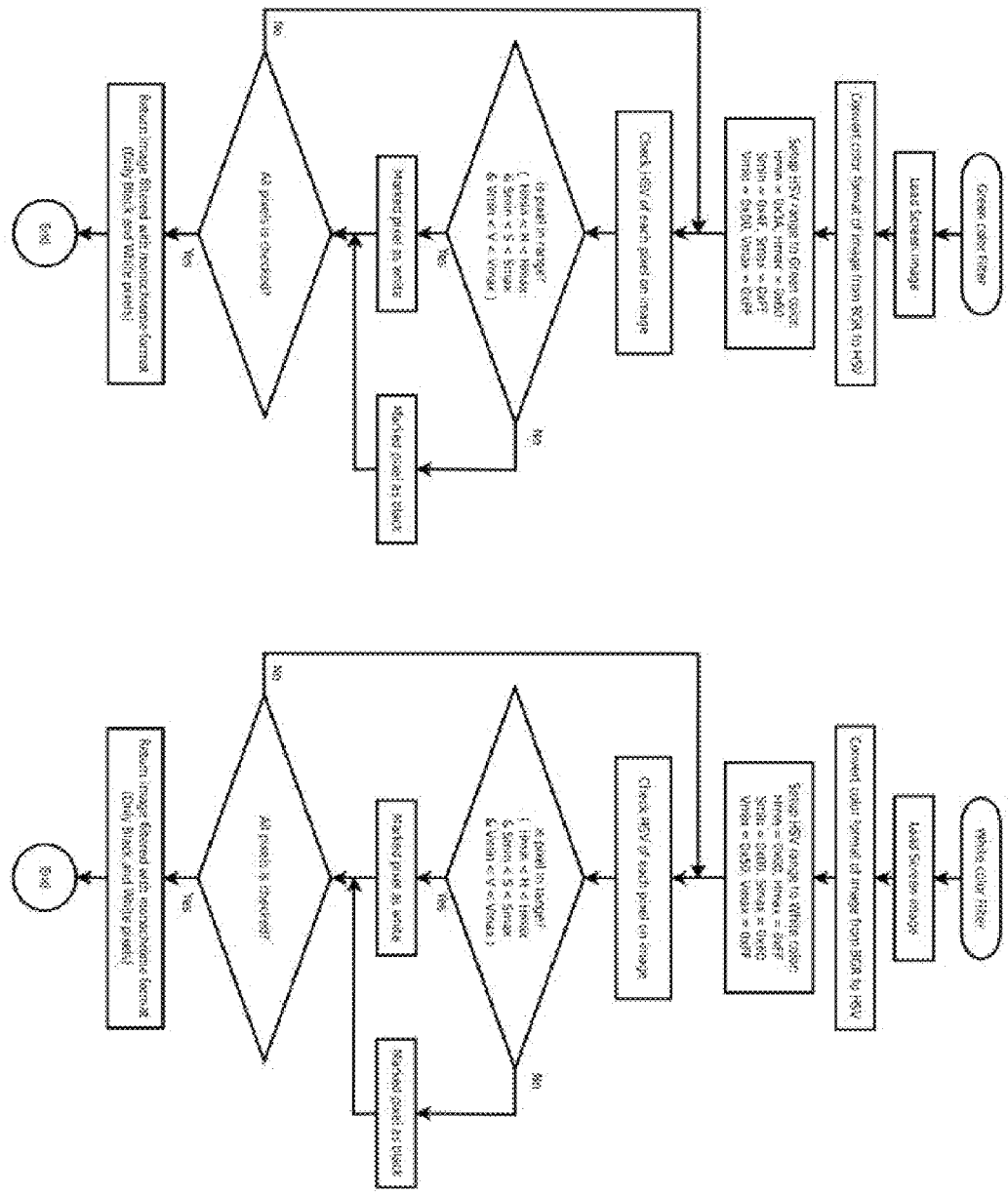
FIG. 11 shows two flowcharts showing the operation of the green and white filters.

FIG. 11 shows a flowchart for applying the white or green filters to the image. As shown in both flowcharts, the screen image is loaded and the color format is converted from RGB to HSV. Then, for the green filter, the HSV range is set to "green", and for the white filter, the HSV range is set to "white". The processor then checks every pixel in the image. If it is within the set HSV range, it is marked as white. If it is outside of the set HSV range, it is marked as black.

It will be understood that while white and green are used as colors in the preferred embodiment of the present invention, it will work with any other colors.

FIG. 12 shows the images at different steps of the process. The top left image is the original image of the screen. A white filter is applied to the image, leading to the bottom left image of the screen, and a green filter is applied, leading to the top middle image of the screen. The two are combined with an OR function, leading to the bottom middle image of the screen. Note that since there is LCD damage, a black area shows up on the image and the system concludes that there is LCD damage. If no black areas were found, the system would conclude that the LCD is undamaged. In the preferred embodiment, the image could be inverted (resulting in the top right image of the screen) and combined with a grid image to show the final result (bottom right image of the screen). The results could then be displayed for the user as shown in the bottom right image.

Figure 13:
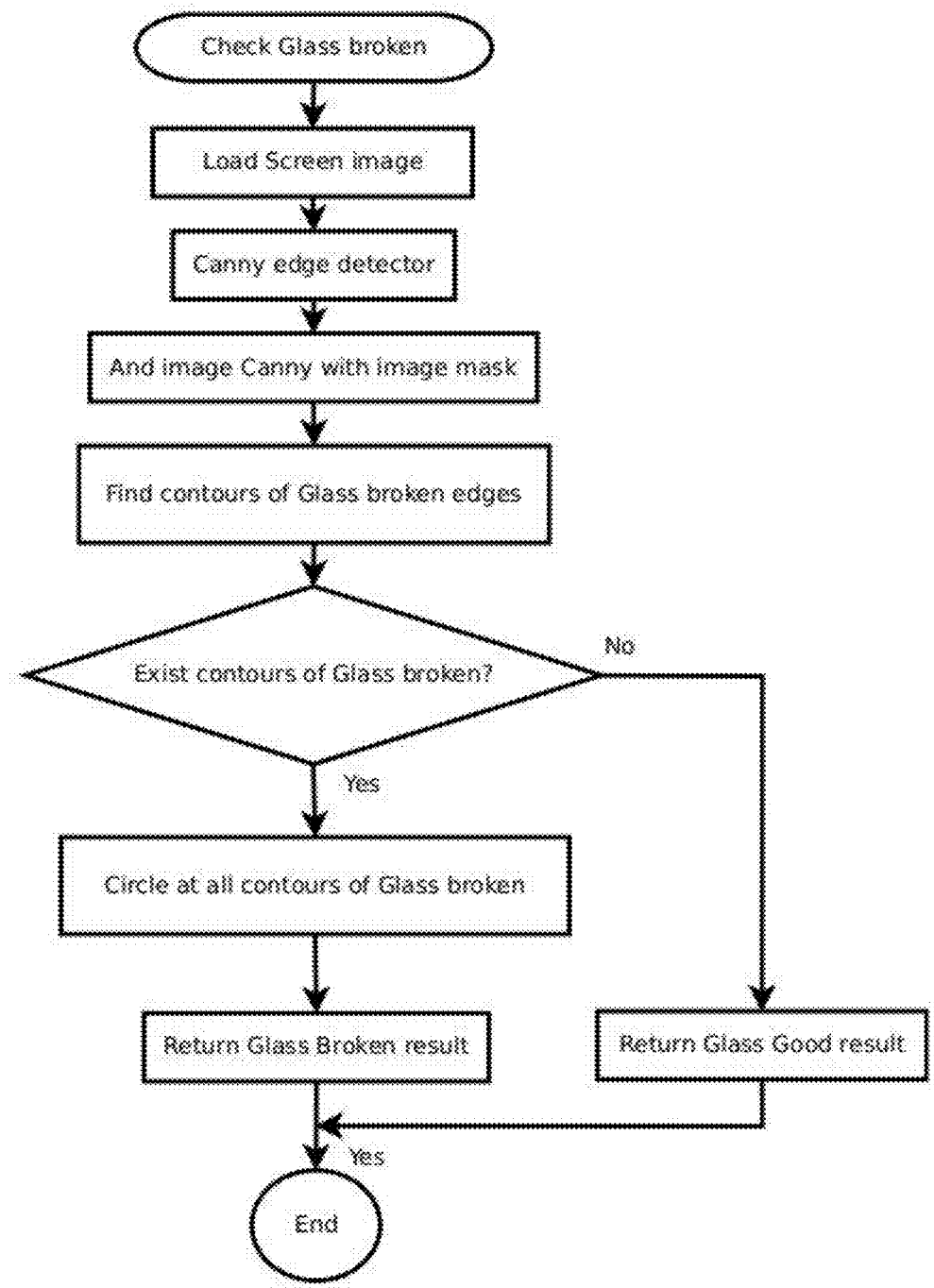
FIG. 13 shows a flowchart showing the process for detecting cracked glass.

FIG. 13 shows a flowchart for determining whether the device has any cracks in the glass. The screen image is loaded. An edge detector algorithm is used on the image to produce an edge image. The edge detector algorithm is preferably the Canny algorithm, but any other edge detector algorithm may be used. Then, a green filter and a white filter are applied to the original image and the green-filtered image and the white-filtered image are added together to produce an image mask. The edge image and the image mask are then added together with an AND function and run through the edge detector again. If any edges are found, they are circled and the system returns a "Cracked glass" result. If no edges are found, the system returns a "Good Glass" result.

FIG. 14 shows a sequence of images illustrating the flowchart above. The top left image is the screen of the electronic device prior to any processing (other than isolating and reshaping into a rectangle). An edge detector algorithm is used to produce the upper middle image. Also, a green filter and a white filter are applied to the image to produce the middle left image and the middle middle image, respectively. Those two images are then added together with an AND function to produce the lower left image, and inverted to produce the lower middle image.

After those steps are done, the lower middle image and the upper middle image are added together with an AND function to produce the upper right image.

Prior to any of these steps, a mask is created by taking the original green and white checked image (with no cracks on it), applying a green filter to it to produce a green-filtered image, applying a white filter to it to produce a white-filtered image, and adding the two with an AND function to produce a mask.

The mask is then added to the upper right image in FIG. 11 with an AND function to produce an image of the cracks as shown in the middle right image. Finally, the cracks (if any) are found and marked, as shown in the lower right image, and a message is displayed on the screen to indicate the electronic device's condition.

The same algorithm is used to detect scratches. In the preferred embodiment, the way that the system detects the difference between scratches and cracks is by looking at the length and extent of the marks detected. If the mark extends all the way to the edge of the screen, it is marked as a crack. If it does not, it is marked as a scratch.

In the preferred embodiment, the results of the analysis are simply displayed on the screen. However, the results may also be transmitted to a server as part of determining the value of an electronic device. The results may be transmitted as raw data (how many scratches, how many cracks, and so on), or processed into a score.

In an embodiment, a cosmetic score is calculated for the device using the number of markings and their length, in each category. Any commonly-known method of calculating a score can be used. For example, the markings can be divided into categories by length—scratches less than 0.5 mm in length, scratches between 0.5 mm and 1 mm in length, scratches between 1 mm and 2 mm in length, and so on. Then, the number of scratches in each category is multiplied by the average length of the scratches in that category, and the products for each category are added together. The result would be the "scratch score". A "crack score" and a "LCD damage score" could be calculated similarly, and the three numbers could be added together, or multiplied by different weighting factors before being added.

While a preferred embodiment of calculating the cosmetic score is described above, any other method of calculating a score based on the cosmetic data could be used.

Exemplary embodiments have been described above. It will be understood that the invention encompasses other embodiments and that the only limitations on the scope of the present invention are expressed in the appended claims.

The invention claimed is:

1. A system for performing a cosmetic evaluation of an electronic device, said system comprising:
   an electronic device, said electronic device comprising a first camera, a screen, and a processor, said electronic device comprising a front side, a back side, a left side, a right side, a top side, and a bottom side;
   a first mirror;
   wherein software is installed on the electronic device to cause the electronic device to perform the following actions:
      trigger the first camera to take a first photograph when the electronic device is placed in front of the first mirror in such a way as to reflect an image of at least one side of the electronic device so that the image is in the first camera's field of view;
      use the processor of the electronic device to analyze the first photograph to determine the location of the electronic device in the first photograph;
      use the processor of the electronic device to crop the first photograph to isolate an image of the electronic device;
      use the processor of the electronic device to analyze the image of the electronic device to determine the number and type of cosmetic imperfections on the at least one side;
      use the processor of the electronic device to produce a report on the cosmetic condition of the electronic device;
   wherein the system does not comprise a processor external to the electronic device;
   wherein the system does not comprise a camera external to the electronic device.

2. The system of claim 1, wherein the processor of the electronic device is further configured to:
   transmit the report to a server.

3. The system of claim 1, wherein the processor of the electronic device is further configured to:
   display the report on the electronic device.

4. The system of claim 1, wherein the electronic device comprises a second camera, and wherein the processor of the electronic device is further configured to:
   trigger the second camera to take a second photograph when the electronic device is placed in front of the first mirror in such a way as to reflect an image of at least one side of the electronic device so that the image is in the second camera's field of view;
   use the processor of the electronic device to analyze the second photograph to determine the location of the electronic device in the second photograph;
   use the processor of the electronic device to crop the second photograph to isolate a second image of the electronic device;
   use the processor of the electronic device to analyze the second image of the electronic device to determine the number and type of cosmetic imperfections on the at least one side.

5. The system of claim 1, further comprising:
   a second mirror, said second mirror placed in such a way relative to the first mirror as to reflect at least one of the right side, left side, top side, or bottom side in such a way that it is in the first camera's field of view;
   wherein the processor of the electronic device is further configured to:
      take a third photograph of the electronic device in such a way that at least one of the right side, left side, top side, or bottom side is visible;
      use the processor of the electronic device to analyze the third photograph to determine the location of the electronic device in the third photograph;
      use the processor of the electronic device to crop the third photograph in such a way as to isolate a third image of the electronic device;
      use the processor of the electronic device to analyze the third image of the electronic device to determine the number and type of cosmetic imperfections on the at least one of the right side, left side, top side, or bottom side.

6. The system of claim 1, wherein the processor of the electronic device is further configured to do one of the following:
   cause the screen of the electronic device to display a static image while the first photograph is taken;
   cause the screen of the electronic device to display a solid color while the first photograph is taken;
   cause the screen of the electronic device to turn off while the first photograph is taken.

7. The system of claim 1, wherein the processor of the electronic device is further configured to:
   display instructions for a user on proper placement of the electronic device in front of the first mirror;
   do one of the following actions:
      take the first photograph automatically when the user places the electronic device correctly;
      instruct the user on when to take the first photograph.

8. A method of performing a cosmetic evaluation of an electronic device, said electronic device having a front side, back side, top side, bottom side, right side, and left side, said electronic device having a first camera, said electronic device having a processor and memory, said method comprising:
   installing an application on the electronic device, wherein the application causes the electronic device to:

trigger the first camera to take a first photograph when the electronic device is placed in front of a mirror in such a way as to reflect an image of at least one side of the electronic device so that the image is in the first camera's field of view;

analyze the first photograph to determine the number and type of cosmetic imperfections on the at least one side;

positioning a first mirror in front of the first camera;

using the first camera to take a first photograph of the at least one side of the electronic device;

determining the location of the electronic device in the first photograph;

cropping the first photograph to isolate a first image of the electronic device;

analyzing the first image of the electronic device to determine the cosmetic condition of the electronic device.

9. The method of claim 8, wherein the electronic device comprises a length L and a height H, wherein the step of using the first camera to take a first photograph comprises:

tilting the electronic device at a tilt angle θ in such a way that the first photograph includes the entire electronic device, wherein the relationship between the tilt angle, the length, and the height is $\tan(\theta) < L/(0.5*H)$.

10. The method of claim 8, wherein the analyzing step is performed by:

changing the contrast on the photograph to make any imperfections more visible;

counting the number of scratches and wear marks in the photograph and determining the length of each imperfection;

using the number of scratches and wear marks and their length to produce a cosmetic condition score.

11. The method of claim 8, where the electronic device further comprises a second camera located on the front side, wherein the application further causes the electronic device to trigger the second camera to take a second photograph of the electronic device when the electronic device is positioned in front of a mirror in such a way as to reflect an image of at least one side of the electronic device so that the image is in the second camera's field of view, further comprising:

positioning the first mirror in front of the second camera;

using the second camera to take a second photograph of at least one side of the electronic device;

determining the location of the electronic device in the second photograph;

cropping the second photograph to isolate a first image of the electronic device;

analyzing the second image of the electronic device to determine the number and type of cosmetic imperfections on the at least one side.

12. The method of claim 8, further comprising:

positioning a second mirror near the electronic device in such a way that at least one of the top side, bottom side, right side, and left side, are reflected in such a way that at least one of the first camera and second camera can photograph the at least one of the top side, bottom side, right side, and left side, resulting in at least one additional photograph;

using the processor of the electronic device to determine the location of the electronic device in the at least one additional photograph;

using the processor of the electronic device to crop the at least one additional photograph to isolate at least one additional image of the electronic device;

analyzing the at least one additional image of the electronic device to determine the determine the number and type of cosmetic imperfections on the at least one of the top side, bottom side, right side, and left side.

13. The method of claim 8, further comprising performing one of the following:

disabling the screen of the electronic device;

causing the screen of the electronic device to display a solid color;

causing the screen of the electronic device to display a static image.

14. The method of claim 13, wherein the analyzing step is performed by:

changing the contrast on the photograph to make any imperfections more visible;

counting the number of scratches and wear marks in the photograph and determining the length of each imperfection;

using the number of scratches and wear marks and their length to produce a cosmetic condition score.

15. The method of claim 8, wherein at least one photograph shows the screen of the device, wherein the electronic device displays a solid white background, wherein the analyzing step comprises:

determining whether the at least one photograph shows any cracks in the screen of the device;

if the at least one photograph shows a crack on the screen of the device, determining whether the display shows any imperfections around the area of the crack;

if the solid white background shows any imperfections around the area of the crack, concluding that the LCD screen of the device is damaged;

if the solid white background shows no imperfections around the area of the crack, concluding that the LCD screen of the device is undamaged.

16. The method of claim 8, where the electronic device displays instructions for a user for the step of placing a mirror in front of the first camera.

17. The method of claim 9, where the electronic device displays instructions for a user for the step of placing a mirror in front of the second camera.

18. The method of claim 17, where the instructions are one or more of the following: auditory, visual, vibratory.

19. The method of claim 8, where the electronic device is triggered to take the first photograph automatically when it is at a predetermined distance from the mirror, said predetermined distance being the closest focal distance for the first camera.

20. The method of claim 8, further comprising:

determining a unique identification for the electronic device;

encoding at least one of the following in the photograph: the unique identification, a time and date of the photograph, a visual parameter of the photograph, or the name of the owner of the electronic device.

21. The method of claim 19, wherein the encoding is done in one or more of the following ways: steganographically, prepended to the image, postpended to the image, encrypted.

22. A method of performing a cosmetic evaluation of an electronic device, said electronic device having a front side, back side, top side, bottom side, right side, and left side, said electronic device having a first camera, said electronic device having a processor and memory, said method comprising:

installing an application on the electronic device, wherein the application causes the electronic device to:

trigger the first camera to take a first photograph when the electronic device is placed in front of a mirror in such a way as to reflect an image of at least one side of the electronic device so that the image is in the first camera's field of view;

analyze the first photograph to determine the number and type of cosmetic imperfections on the at least one side;

positioning a first mirror in front of the first camera;

using the first camera to take a first photograph of the at least one side of the electronic device;

analyzing the first photograph to determine the cosmetic condition of the electronic device:

wherein the at least one photograph shows the screen of the electronic device, wherein the electronic device displays a background image comprising areas of a first color and areas of a second color, wherein the analyzing step comprises:

creating an image mask, which comprises the following steps:
  applying a filter of the first color to the background image to create a first color-filtered background image;
  applying a filter of the second color to the background image to create a second color-filtered background image;
  merging the first color-filtered background image and the second color-filtered background image and inverting to create an image mask;

identifying and isolating the screen of the electronic device in the at least one photograph to produce a screen image;

using an edge detector algorithm to create a processed screen image;

applying a colored filter of the first color to the screen image to produce a first color-filtered screen image;

applying a colored filter of the second color to the screen image to produce a second color-filtered screen image;

merging the first color-filtered screen image and the second color-filtered screen image and inverting the result to produce a merged screen image;

merging the merged screen image and the processed screen image and subtracting the mask image to produce a result image;

applying an edge detector algorithm to the result image;

if any edges are found, circling them on the display of the electronic device and concluding that the electronic device has a scratch or a crack.

23. The method of claim 22, further comprising:
for each edge, determining whether or not it extends to an outer edge of the image;
if an edge extends to the outer edge of the image, concluding that the electronic device has a crack;
if an edge does not extend to the outer edge of the image, concluding that the electronic device has a scratch.

24. A method of performing a cosmetic evaluation of an electronic device, said electronic device having a front side, back side, top side, bottom side, right side, and left side, said electronic device having a first camera, said electronic device having a processor and memory, said method comprising:

installing an application on the electronic device, wherein the application causes the electronic device to:
  trigger the first camera to take a first photograph when the electronic device is placed in front of a mirror in such a way as to reflect an image of at least one side of the electronic device so that the image is in the first camera's field of view;
  analyze the first photograph to determine the number and type of cosmetic imperfections on the at least one side;

positioning a first mirror in front of the first camera;

using the first camera to take a first photograph of the at least one side of the electronic device;

analyzing the first photograph to determine the cosmetic condition of the electronic device, wherein the at least one photograph shows the screen of the electronic device, wherein the electronic device displays a background image comprising areas of a first color and areas of a second color, wherein the analyzing step comprises:

identifying and isolating the screen of the electronic device in the at least one photograph to produce a screen image;

applying a colored filter of the first color to the screen image to produce a first color-filtered screen image;

applying a colored filter of the second color to the screen image to produce a second color-filtered screen image;

merging the first color-filtered screen image and the second color-filtered screen image with an OR function to create a merged image;

if any pixels in the merged image are black, concluding that the electronic device has a damaged LCD screen.

* * * * *